(12) United States Patent
Kang et al.

(10) Patent No.: US 12,351,586 B2
(45) Date of Patent: Jul. 8, 2025

(54) THIOPHENE[2,3-D]PYRIMIDINE DERIVATIVE DK6-1 AND ITS PREPARATION METHOD AND APPLICATION

(71) Applicant: SHAN DONG UNIVERSITY, Jinan (CN)

(72) Inventors: Dongwei Kang, Jinan (CN); Xinyong Liu, Jinan (CN); Peng Zhan, Jinan (CN)

(73) Assignee: SHAN DONG UNIVERSITY, Jinan (CN)

(*) Notice: Subject to any disclaimer, the term of this patent is extended or adjusted under 35 U.S.C. 154(b) by 536 days.

(21) Appl. No.: 17/757,821

(22) PCT Filed: Mar. 3, 2020

(86) PCT No.: PCT/CN2020/077564
§ 371 (c)(1),
(2) Date: Jun. 21, 2022

(87) PCT Pub. No.: WO2021/164052
PCT Pub. Date: Aug. 26, 2021

(65) Prior Publication Data
US 2023/0067045 A1      Mar. 2, 2023

(30) Foreign Application Priority Data
Feb. 21, 2020 (CN) .......................... 202010105624.5

(51) Int. Cl.
C07D 495/04     (2006.01)
A61P 31/18      (2006.01)

(52) U.S. Cl.
CPC ............ *C07D 495/04* (2013.01); *A61P 31/18* (2018.01)

(58) Field of Classification Search
CPC ............................... C07D 495/04; A61P 31/18
See application file for complete search history.

(56) References Cited

PUBLICATIONS

Huo et al., ACS Med. Chem. Lett. 334-338 (2018) (Year: 2018).*

\* cited by examiner

*Primary Examiner* — Timothy R Rozof
(74) *Attorney, Agent, or Firm* — CBM PATENT CONSULTING, LLC

(57) ABSTRACT

The present invention belongs to the field of pharmaceutical technology, specifically disclosing a class of thienopyrimidine compounds with the general formula I, theirs stereoisomeric forms, stereoisomeric mixtures and pharmaceutically acceptable salts, hydrates and solvents. Also including theirs polycrystalline and eutectic, prodrugs and derivatives with same biologically functional, methods for their preparation, and compositions containing one or more of these compounds in the drugs application of treatment and prevention of human immunodeficiency virus (HIV).

15 Claims, 1 Drawing Sheet

THIOPHENE[2,3-D]PYRIMIDINE DERIVATIVE DK6-1 AND ITS PREPARATION METHOD AND APPLICATION

FIELD OF THE INVENTION

The present invention relates to the field of organic compound synthesis and pharmaceutical applications, and more particularly to thiophene[2,3-d]pyrimidine derivative DK6-1 and its preparation method and as an application of HIV-1 inhibitor.

BACKGROUND OF THE INVENTION

Acquired Immune Deficiency Syndrome (AIDS) has become a major infectious disease endangering human life and health at present, and its main pathogen is human immunodeficiency virus type 1 (HIV-1). Although the implementation of highly active antiretroviral therapy (HAART) significantly prolonged the survival of patients, the problems of drug resistance, serious side effects and long-term drug costs forcing researchers to develop novel HIV-1 inhibitors with higher potency and lower toxicity. HIV-1 non-nucleoside reverse transcriptase inhibitors (NNRTIs) have gained an increasingly important role in highly active antiretroviral therapy (HAART) regimens used to treat AIDS patients for their potent antiviral activity, high selectivity, and lack of mitochondrial toxicity which characterizes the NRTIs. However, drug-resistant mutants rapidly emerge with their clinical applications because of their allosteric mechanism of action and low genetic barrier. Therefore, the development of novel high-efficiency and low-toxicity NNRTIs has always been one of the hot spots of anti-HIV drug research.

Diarylpyrimidine (DAPY) is a typical class of HIV-1 NNRTIs, which has effective activity against wild-type and mutant HIV-1 strains. Up to now, two DAPY NNRTIs etravirine (ETV) and rilpivirine (RPV) have been approved by the U.S. FDA. However, these compounds have poor water solubility and led to their low oral bioavailability. With ETR and RPV as the lead compounds, our previous efforts have led to the design and synthesis of two novel NNRTIs K-5a2 和 25a. However, both compounds suffered from a stronger human ether-a-go-go related gene (hERG) inhibitory activity (K-5a2, $IC_{50}$=0.130 μM; 25a, $IC_{50}$=0.186 μM). In addition, 25a showed higher cytotoxicity ($CC_{50}$=2.30 μM) and lower bioavailability (F=16.19%). Therefore, further structure modification is still needed to achieve improved antiviral potency, decreased toxicity, and favorable pharmacokinetic properties.

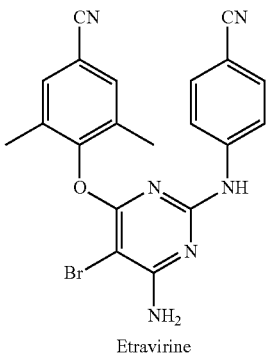

Etravirine

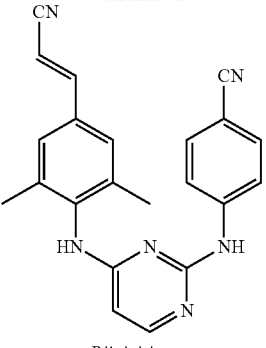

Rilpivirine

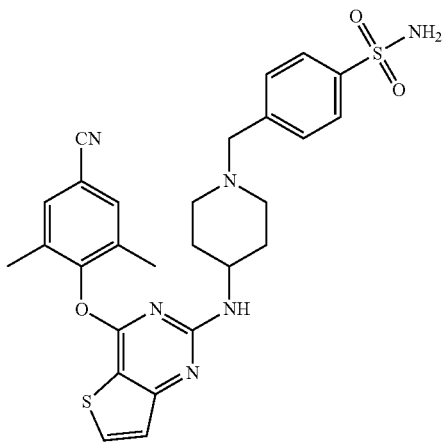

K-5a2

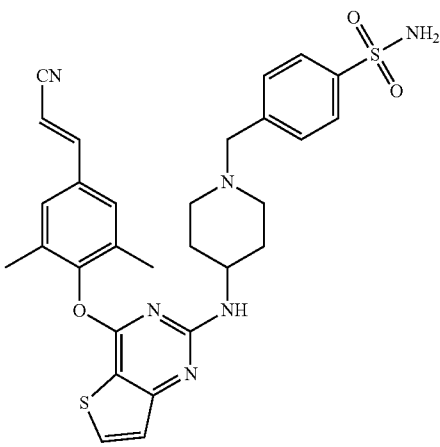

25a

SUMMARY OF THE INVENTION

The present invention provides a thiophene[2,3-d]pyrimidine derivative DK6-1 and a preparation method thereof. The invention also provides the use of thiophene[2,3-d] pyrimidine derivative DK6-1 as HIV-1 inhibitor.

The technical proposal of the invention is as follows:

1. Thiophene[2,3-d]pyrimidine Derivative DK6-1

The invention provides thiophene[2,3-d]pyrimidine derivative DK6-1, and pharmaceutically acceptable salt, ester or prodrug thereof.

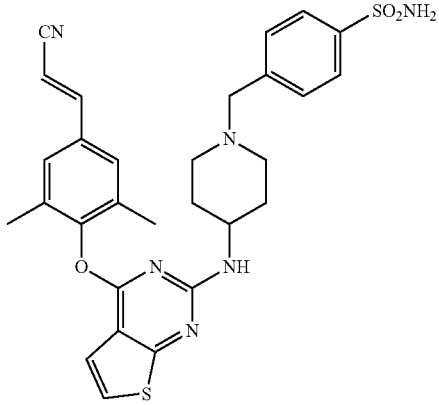

DK6-1

2. Preparation of Thiophene[2,3-d]pyrimidine Derivative DK6-1

The preparation method of thiophene[2,3-d]pyrimidine derivative DK6-1 is as follows: the commercially available 2,4-dichlorothiophene[2,3-d]pyrimidine (1) was selected as starting material, which was treated with 3,5-dimethyl-4-hydroxybenzaldehyde afforded intermediate 2. The cyanovinyl compound 3 was obtained by reaction of 2 with diethyl cyanomethylphosphonate under Wittig-Horner reaction. Then 3 was treated with N-(tert-butoxycarbonyl)-4-aminopiperidine and trifluoroacetic acid to yield the key intermediate 4, which was reacted with 4-(bromomethyl)benzenesulfonamide to give the target compound DK6-1.

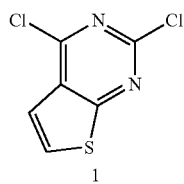

1

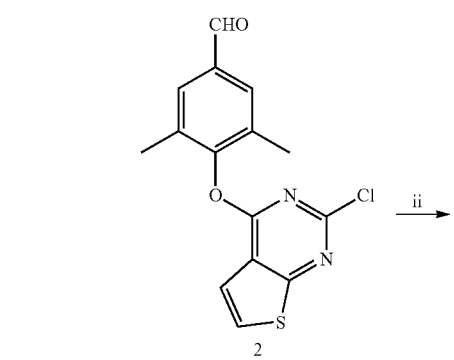

2

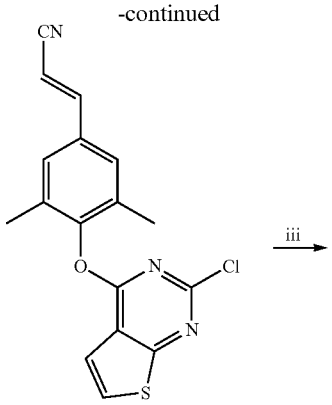

3

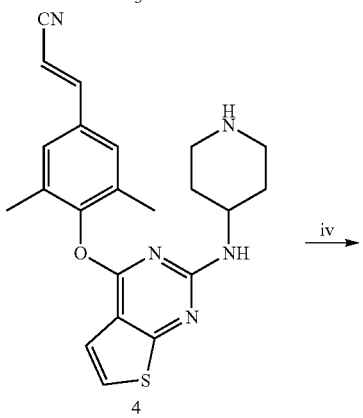

4

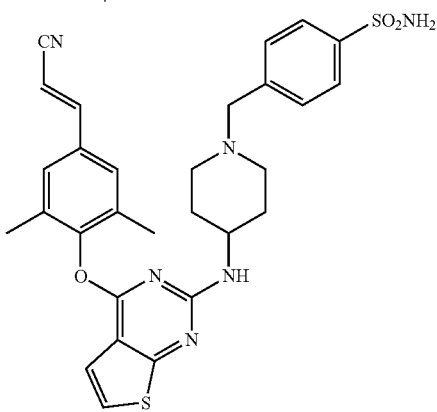

DK6-1

Reagents and conditions: (i) 3,5-dimethyl-4-hydroxybenzaldehyde, DMF, $K_2CO_3$, 20-30° C.; (ii) $(EtO)_2P(O)CH_2CN$, t-BuOK, THF/DCM, 0° C.; (iii) 4-(tert-butoxycarbonyl)aminopiperidine, DMF, $K_2CO_3$, reflux; then TFA, DCM, 20-30° C.; (iv) 4-(bromomethyl)benzenesulfonamide, DMF, $K_2CO_3$, 20-30° C.

3. Activity Evaluation and Application of Thiophene[2,3-d]pyrimidine Derivative DK6-1

Antiviral potency was evaluated in MT-4 cell cultures infected with WT HIV-1 strain (IIIB) as well as cells infected with a panel of NNRTI-resistant single- and double-mutant strains, such as L100I, K103N, Y181C, Y188L, E138K, F227L+V106A and K103N+Y181C (RES056). Etravirine (ETR) was selected as control drug.

The values of $EC_{50}$ (anti-HIV activity) and $CC_{50}$ (cytotoxicity) was depicted in FIG. 1. DK6-1 showed potent activity against wild-type and mutant HIV-1 strains, being superior to that of ETR. For HIV-1 wild-type and K103N mutant strains, DK6-1 exhibited an $EC_{50}$ values of 3.24 nM and 2.34 nM, being comparable to that of ETR; for L100I, Y181C, Y188L and E138K, DK6-1 was demonstrated with $EC_{50}$ values less than 8 nM, being 2-fold more potent than that of ETR; in the case of F227L+V106A and RES056, the activity of DK6-1 was 6-fold and 3-fold potent than that of ETR, respectively. Moreover, the cytotoxicity of DK6-1 ($CC_{50}$=10.1 μM) was much decreased compared to that of 25a ($CC_{50}$=2.30 μM).

Then, MT-4 cells infected with HIV-1 IIIB was passaged for 30 times in the presence of DK6-1. Several mutations were detected in the RT gene in comparison with the DNA sequence of the WT HIV-1 (IIIB) strain, including K101E, V108I, F227C, and M230I. The activities of DK6-1 against these mutant strains sharply decreased compared to its activity against HIV-1 IIIB, but he NRTIs AZT exhibited significantly higher potency against these mutant strains ($EC_{50}$=1.0 nM), being about 10-fold potent than its activity against HIV-1 IIIB ($EC_{50}$=12.7 nM). The distinct antiviral resistance profiles of the novel discovered NNRTIs DK6-1 and the approved NRTIs AZT support the use of them together in HAART and should be helpful in the development of next generation of anti-HIV therapy with an increased genetic barrier to resistance.

The pharmacokinetics study result (FIG. 1) demonstrated that DK6-1 have a favorable bioavailability (F=37.06%) and better safety profiles ($LD_{50}$>2000 mg/kg). The hERG inhibitory activity result indicated that DK6-1 exhibited much reduced QT liability and lower hERG inhibition ($IC_{50}$=0.98 μM) in comparison with that of 25a ($IC_{50}$=0.186 μM) and K-5a2 ($IC_{50}$=0.130 μM). The promising in vitro and in vivo results highlights that DK6-1 has enormous potential as a next generation anti-HIV-1 drug candidate.

Also described here are thiophene[2,3-d]pyrimidine derivative DK6-1 used as HIV-1 NNRTIs, furthermore, these HIV-1 inhibitors will be used as anti-AIDS drugs.

Also described here are pharmaceutical composition comprising thiophene[2,3-d]pyrimidine derivative DK6-1, and with one or more kind of pharmaceutically acceptable carrier or excipient The present invention provides a novel thiophene[2,3-d]pyrimidine derivative DK6-1, its preparation method, anti-HIV-1 activity screening result and its first application in the field of antiviral. The thiophene[2,3-d]pyrimidine derivative DK6-1 of the present invention have been proved to be useful as HIV-1 inhibitor and have high application value. In particular, it can be used as anti-AIDS drug.

EXAMPLES

Figure 1:
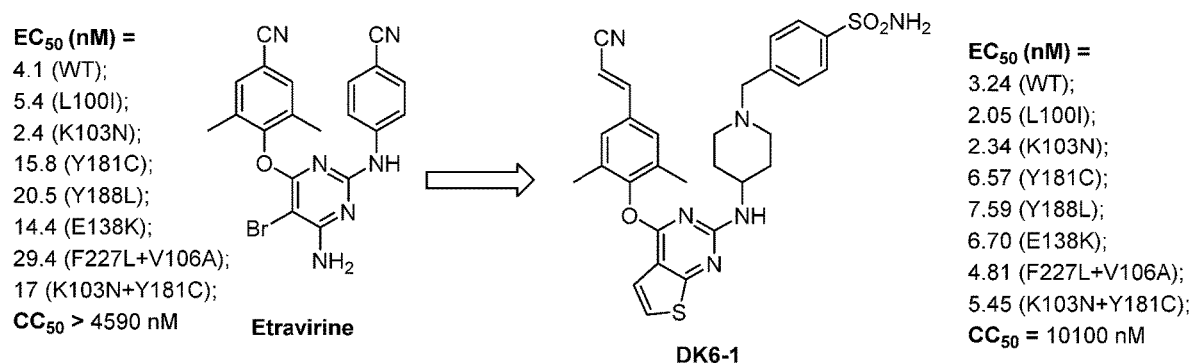
FIG. 1 shows the comparison of cell activity and cytotoxicity between ETR and DK6-1.

Selected examples are listed as follows, the invention includes these compounds disclosed herein but not confined to them.

Example 1

The Preparation of (E)-3-(3,5-dimethyl-4-((2-(piperidin-4-ylamino)thieno[2,3-d]pyrimidin-4-yl)oxy)phenyl)acrylonitrile (4)

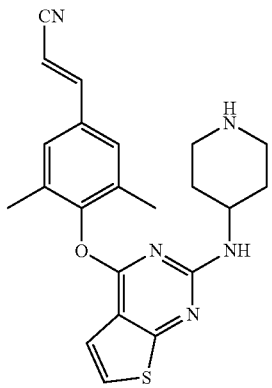

A mixture of 4-hydroxy-3,5-dimethylbenzaldehyde (1.76 g, 11.7 mmol) and $K_2CO_3$ (2.70 g, 19.5 mmol) in 40 mL of DMF was stirred at room temperature for 15 min, and then 2,4-dichlorothiopheno[2,3-d]pyrimidine (1, 2.0 g, 9.76 mmol) was added to the mixture. The mixture was stirred for another 1.5 h and then poured into ice water (200 mL) and left to stand for 20 min. The obtained precipitated was filtrated and washed with cold water, recrystallized from DMF-$H_2O$ to provide intermediate 2 as a white solid in 85% yield, mp: 263-265° C. ESI-MS: m/z 319.4 (M+1), 341.2 (M+Na). $C_{15}H_{11}ClN_2O_2S$ (318.02).

A mixture of $(EtO)_2P(O)CH_2CN$ (1.34 g, 7.52 mmol) and t-BuOK (1.42 g, 12.5 mmol) in THF (25 mL) was stirred for 1 h at 0° C., and then a solution of 2(2.0 g, 6.28 mmol) in THF (15 mL) and DCM (15 mL) was slowly added over 1 h. The mixture was stirred for another 4 hours at room temperature and then poured into ice water (60 mL). The precipitate was collected and washed with water to give intermediate 3 as a white solid in 72% yield, mp: 235-237° C. ESI-MS: m/z 342.4 (M+1), 364.2 (M+Na). $C_{17}H_{12}ClN_3OS$ (341.04).

Compound 3 (0.34 g, 1.0 mmol), N-Boc-4-aminopiperidine (0.24 g, 1.2 mmol), and anhydrous $K_2CO_3$ (0.28 g, 2 mmol) were added in DMF (10 mL) and refluxing 8 h under magnetic stirring (monitored by TLC). Then the mixed solution was cooled to room temperature and 50 mL of ice water was added. The resulting precipitate was collected and dissolved in DCM (5 mL) and trifluoroacetic acid (TFA) (0.74 mL, 10 mmol). The mixed solution was stirred for another 3 h (monitored by TLC) at room temperature. Then the reaction solution was alkalized to pH 9 with saturated sodium bicarbonate solution and washed with saturated sodium chloride solution (10 mL). The aqueous phase was extracted with DCM (3×5 mL). Then the combined organic phase was dried over anhydrous $Na_2SO_4$, filtered, and concentrated under reduced pressure to give 4 as a white solid in 71% yield, mp 123-125° C. ESI-MS: m/z 406.3 (M+1). $C_{22}H_{23}N_5OS$ (405.16).

Example 2

The Preparation of DK6-1

Compound 4 (0.20 g, 0.5 mmol) and anhydrous $K_2CO_3$ (0.14 g, 1.0 mmol) were added to anhydrous DMF (10 mL), which was followed by addition of 4-(bromomethyl)benzenesulfonamide (0.15 g, 0.6 mmol). The reaction mixture was stirred at room temperature for 6 h (monitored by TLC). Then the solvent was removed under reduced pressure, and water (30 mL) was added, extracted with ethyl acetate (3×10 mL), and the organic phase was washed with saturated sodium chloride (10 mL), then dried over anhydrous $Na_2SO_4$ to give the corresponding crude product, which was purified by flash column chromatography and recrystallized from ethyl acetate (EA)/petroleum ether (PE) to afford the target compound DK6-1. White solid in 67% yield, mp 205-207° C. $^1$H NMR (400 MHz, DMSO-$d_6$) δ 7.78 (d, J=8.2 Hz, 2H, $C_3,C_5$-Ph'-H), 7.61 (d, J=13.6 Hz, 1H, ArCH=), 7.48-7.45 (m, 4H), 7.35 (d, J=5.9 Hz, 1H, $C_7$-thienopyrimidine-H), 7.31 (s, 2H, $SO_2NH_2$), 7.25 (d, J=6.0 Hz, 1H, $C_6$-thienopyrimidine-H), 7.07 (s, 1H, NH), 6.43 (d, J=16.7 Hz, 1H, =CHCN), 3.72-3.70 (m, 1H), 3.49 (s, 2H, N—$CH_2$), 2.74-2.72 (m, 2H), 2.08 (s, 6H), 1.99-1.27 (m, 6H). $^{13}$C NMR (100 MHz, DMSO-$d_6$) δ 162.6, 159.3, 150.5, 143.4, 143.1, 131.7, 131.7, 129.4, 128.6, 126.0, 119.4, 118.9, 96.7, 62.0, 60.2, 52.7, 31.6, 21.1, 16.6, 14.5. ESI-MS: m/z 575.3 (M+1), 597.5 (M+Na). $C_{29}H_{30}N_6O_3S_2$ (574.18).

Example 3

In Vitro Anti-HIV Activity of DK6-1

Selected compounds were screened for inhibitory activity against HIV-1 using MTT method as describe previously by Christophe. Pannecouque et al. *Nat. Protoc.* 3 (2008) 427-434, and Rudi Pauwels et al. *J. Virol. Methods* 20(1988) 309-321. And in vitro anti-HIV activity of compounds were supported by Rega Institute for Medical Research. The MTT assay is based on the reduction of the yellow colored 3-(4,5-dimethylthiazol-2-yl)-2,5-diphenyltetrazolium bromide (MTT) by mitochondrial dehydrogenases of metabolically active cells to a blue formazan which can be measured spectrophotometrically. Tested optical density served as an indicator for live cells, and survival rate can be concluded by testing the optical density of 540 nm and 690 nm. MT-4 cells infected with HIV-1 can only survive for 5 to 7 days without any treatment, but when HIV-1 inhibitors were added, they can protect MT-4 cell from cytopathic. Serial solution of compounds was added to MT-4 cells after infected with HIV-1, MTT method was used to detect the survival rate after culture for 5 to 7 days. $EC_{50}$ value was defined as compound concentration required to achieve 50% protection of MT-4 cells against HIV-1-induced cytopathic effect.

Materials (1) MT-4 cells infected with HIV-1 viral strains (IIIB, K103N, Y181C, Y188L, Y181C/K103N) were provided by Rega Institute for Medical Research, Katholieke Universiteit Leuven, Belgium.
(2) MTT and formazan: sigma Chemical Co.
(3) Preparation of compounds: Stock solutions (10×final concentration) of test compounds is diluted with double distilled $H_2O$ for 5 folds and 5 concentrations of one compound are prepared.
(4) Reference drug: Etravirine (ETR).
(5) Test method (MTT method): Serial five-fold dilutions of test compounds were added to cultured MT-4 cells infected with HIV-1, after 5 to 7 days, MTT was added and cultured for a few hours. Medium was removed and lysate was added followed by formazan, OD value was determined in 690 nm and 540 nm by microplate reader, and $EC_{50}$ value was calculated.

Methods

The MTT method was described briefly as follows: 96-well plastic microtiter trays were filled with 100 μL of complete medium. Subsequently, serial of tested compounds was added (25 μL) to two series of triplicate wells so as to allow simultaneous evaluation of their effects on HIV- and mock infected cells. 50 μL of 1×10$^4$ cells/mL MT-4 cells were added. After cultured for 5 days at 37° C. in humidified atmosphere in the presence of 5% $CO_2$, MTT was added and cultured for another 2 h, then medium was removed and 100 μL isopropanol solution was added to lyse the cells. Formazan crystals were added and vibrated platform shaker for 10 min to solubilize the formazan crystals. Absorbances at 690 nm and 540 nm were read by using spectrophotometrically. $EC_{50}$ was defined as the concentration achieving 50% protection from the cytopathic effect of the virus in infected cells. The results are shown in FIG. 1.

Example 4

Pharmacokinetics Assays of DK6-1

Ten male Wistar rats (180-200 g) were randomly divided into two groups to receive intravenous (2 mg·kg$^{-1}$) and oral administration (20 mg·kg$^{-1}$) of the compounds. A solution of DK6-1 was prepared by dissolving in polyethylene glycol (peg) 400/normal saline (65/35, V/V). Blood samples of the intravenous group were collected from the jugular sinus at 2 min, 5 min, 15 min, 30 min, 1 h, 1.5 h, 2 h, 4 h, and 8 h after dosing, and blood samples of the oral administration group were collected at 5 min, 15 min, 30 min, 1 h, 2 h, 4 h, 6 h, 8h, 10 h, and 12 h after dosing (200 μL of blood each times). All the samples were then centrifuged at 8000 rpm for 8 min to separate plasma. The concentration of DK6-1 in plasma was determined by LC-MS/MS analysis. Briefly, 50 μL of plasma was added to 50 μL of internal standard and 300 μL of methanol in a 5 mL centrifugation tube, which was centrifuged at 3000 g for 10 min. The supernatant layer was collected and a 20 μL aliquot was injected for LC-MS/MS analysis. Standard curves for DK6-1 in blood were generated by the addition of various concentrations of DK6-1 together with internal standard to blank plasma. Then all samples were quantified with an Agilent 1200 LC/MSD (Agilent, USA). The mobile phase was methanol/1.5% glacial acetic acid (60:40, V/V) at a flow rate of 1.0 mL/min.

The plasma pharmacokinetic data were analyzed by using the non-av model of DAS 2.0 pharmacokinetic program. The main pharmacokinetic parameters (Cmax, AUC, $T_{max}$, $T_{1/2}$, and CL) were calculated. The results are shown in Table 1.

TABLE 1

| | | | | Pharmacokinetics evaluation of DK6-1 | | | |
|---|---|---|---|---|---|---|---|
| Subject | $T_{1/2}$ (h) | $T_{max}$ (h) | $C_{max}$ (ng/mL) | $AUC_{0-t}$ (h*ng/mL) | $AUC_{0-\infty}$ (h*ng/mL) | CL (L/h/kg) | F (%) |
| DK6-1 (iv) | 2.0 ± 0.4 | 0.033 | 1713 ± 399 | 814 ± 179 | 887 ± 174 | 2.3 ± 0.4 | — |
| DK6-1 (po) | 2.8 ± 0.3 | 3.2 ± 0.9 | 614 ± 249 | 3017 ± 547 | 3287 ± 517 | — | 37.06 |

Example 5

Assay Procedures for hERG Activity

The inhibitory activity against the hERG potassium channel was tested in HEK293 cells which were stably transfected with hERG cDNA[26]. HEK239 cells expressing hERG were cultured in 35 mm dishes for 24 hours and kept at 37° C. under 5% $CO_2$. A micropipette was drawn out from borosilicate glass to give a tip resistance between 3~5 MΩ. For each trial, one dish of cells was removed from the incubator, washed twice and placed on the microscope. The whole-cell recordings were performed using a commercial patch clamp amplifier.

Figure 2:
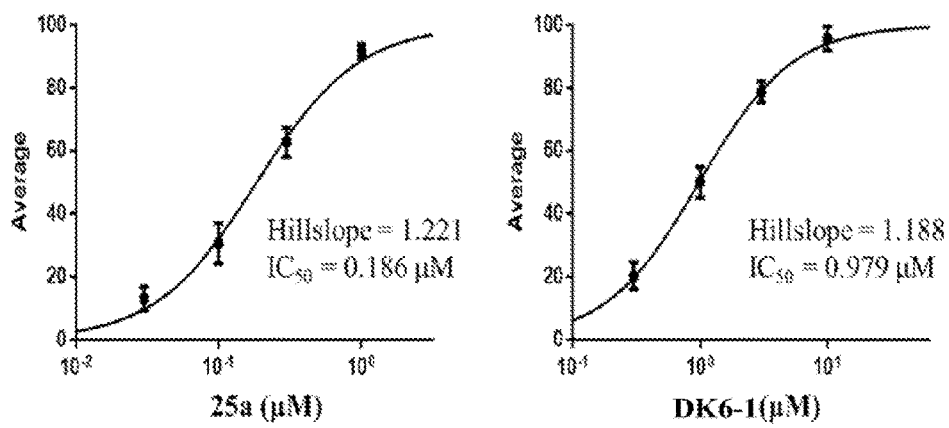
FIG. 2 shows the comparison of hERG inhibitory activity between 25a and DK6-1.

Tail currents were evoked once every 30 s by a 3 s, −50 mV repolarizing pulse following a 2 s, +50 mV depolarizing pulse with a stable voltage of −80 mV. The voltage protocol started with a 50 ms depolarization pulse of −50 mv, which served as the baseline for calculating the peak tail current amplitude. Only stable cells with recording parameters exceeding the threshold were used in the experiments. The hERG current was allowed to stabilize for 3 minutes. The cells were kept in the test solution until the peak tail current was stable (<5% change) for ~5 sweeps. Peak tail amplitudes were then plotted as a function of the sweep number. Before testing the composite application, the average of the five peak tail currents in the steady state was taken as the control current amplitude. Four or five peak tail current measurements at the steady state after test compound application were averaged as the residual current amplitude after the test compound was suppressed. The result is shown in FIG. 2.

What is claimed is:

1. A thiophene[2,3-d] pyrimidine HIV-1 NNRTIs DK6-1 is thiophene[2,3-d] pyrimidine derivative DK6-1, and pharmaceutically acceptable salt, ester or prodrug thereof, wherein the structure of the compound DK6-1 as shown below:

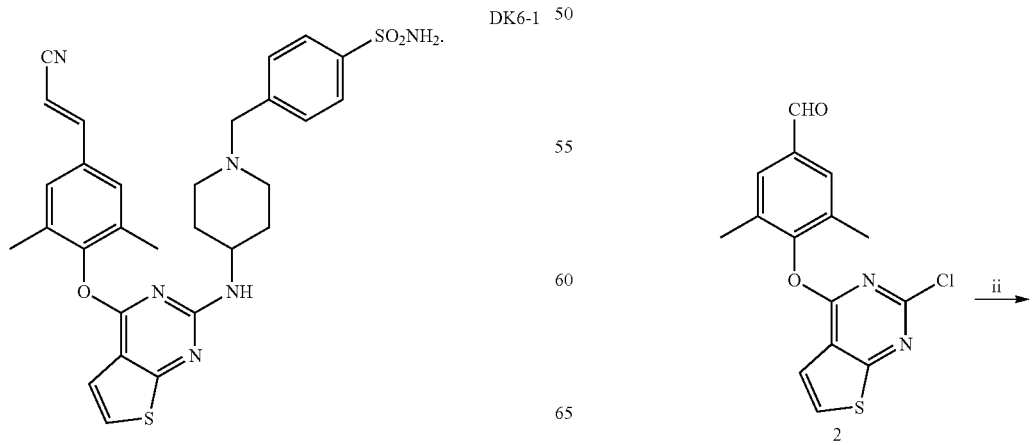

DK6-1

2. The thiophene[2,3-d] pyrimidine HIV-1 NNRTIs DK6-1 of claim 1 is characterized in that the pharmaceutical acceptable salts of the compound are hydrochloride, sulfate, tartrate, citrate, and the pharmaceutical acceptable prodrugs or derivatives of DK6-1.

3. The thiophene[2,3-d]pyrimidine HIV-1 NNRTIs DK6-1 of claim 1 is characterized in that the melting point of DK6-1 is 205-207° C.

4. The thiophene[2,3-d]pyrimidine HIV-1 NNRTIs DK6-1 of claim 1 is characterized in that the spectrum data of DK6-1 are as follows: $^1$H NMR (400 MHz, DMSO-$d_6$) δ 7.78 (d, J=8.2 Hz, 2H, $C_3,C_5$-Ph'-H), 7.61 (d, J=13.6 Hz, 1H, ArCH=), 7.48-7.45 (m, 4H), 7.35 (d, J=5.9 Hz, 1H, $C_7$-thienopyrimidine-H), 7.31 (s, 2H, $SO_2NH_2$), 7.25 (d, J=6.0 Hz, 1H, $C_6$-thienopyrimidine-H), 7.07 (s, 1H, NH), 6.43 (d, J=16.7 Hz, 1H, =CHCN), 3.72-3.70 (m, 1H), 3.49 (s, 2H, N—$CH_2$), 2.74-2.72 (m, 2H), 2.08 (s, 6H), 1.99-1.27 (m, 6H); $^{13}$C NMR (100 MHz, DMSO-$d_6$) δ 162.6, 159.3, 150.5, 143.4, 143.1, 131.7, 131.7, 129.4, 128.6, 126.0, 119.4, 118.9, 96.7, 62.0, 60.2, 52.7, 31.6, 21.1, 16.6, 14.5, ESI-MS: m/z 575.3 (M+1), 597.5 (M+Na) and $C_{29}H_{30}N_6O_3S_2$ (574.18).

5. The thiophene[2,3-d]pyrimidine HIV-1 NNRTIs DK6-1 of claim 1 is characterized by the reaction route as follows:

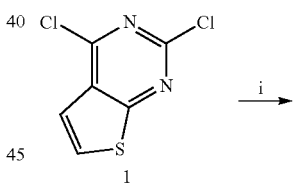

i

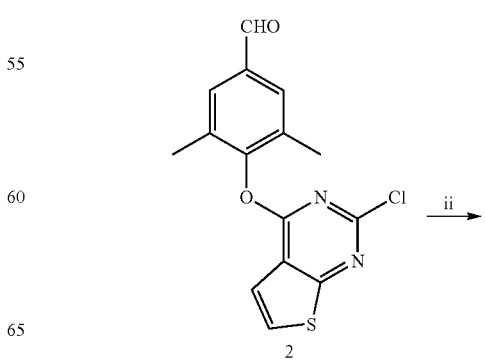

ii

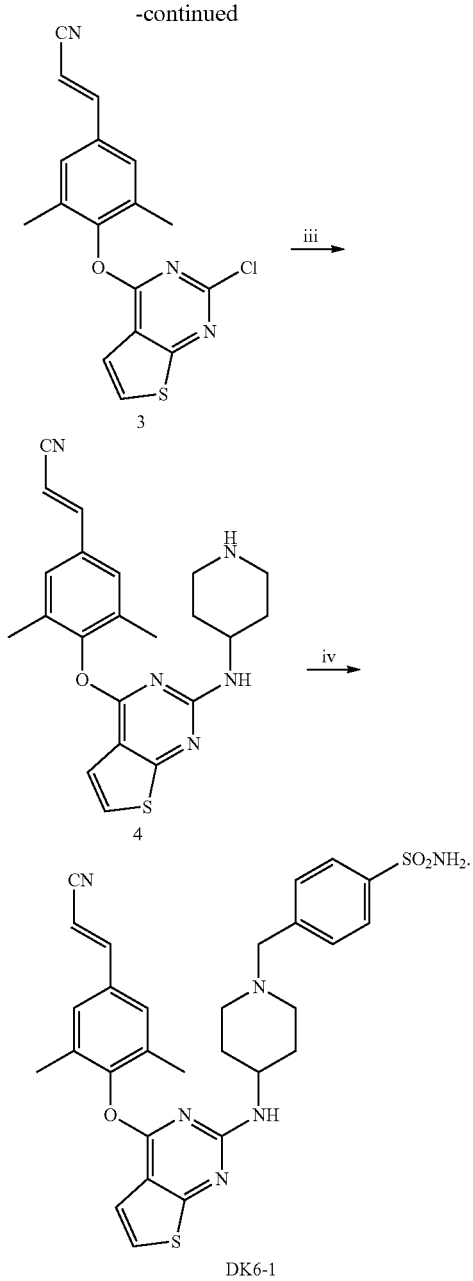

6. A preparation method of thiophene[2,3-d]pyrimidine HIV-1 NNRTIs DK6-1 described in claim 5 is characterized by the reaction route, reagents and conditions as follows:
(i) 3,5-dimethyl-4-hydroxybenzaldehyde, DMF, $K_2CO_3$, 20-30° C.; (ii) $(EtO)_2P(O)CH_2CN$, t-BuOK, THF/DCM, 0° C.; (iii) 4-(tert-butoxycarbonyl)aminopiperidine, DMF, $K_2CO_3$, 120° C.; then TFA, DCM, 20-30° C.; (iv) 4-(bromomethyl)benzenesulfonamide, DMF, $K_2CO_3$, 20-30° C.

7. The preparation method of thiophene[2,3-d]pyrimidine HIV-1 NNRTIs DK6-1 described in claim 6 is characterized by the following steps:
the 2,4-dichlorothiophene[2,3-d]pyrimidine (1) was selected as starting material, which was treated with 3,5-dimethyl-4-hydroxybenzaldehyde afforded intermediate 2, the cyanovinyl compound 3 was obtained by reaction of 2 with diethyl cyanomethylphosphonate under Wittig-Horner reaction; then 3 was treated with N-(tert-butoxycarbonyl)-4-aminopiperidine and trifluoroacetic acid to yield the key intermediate 4, which was reacted with 4-(bromomethyl)benzenesulfonamide to give the target compound DK6-1.

8. The thiophene[2,3-d]pyrimidine HIV-1 NNRTIs DK6-1 of claim 1, wherein the thiophene[2,3-d]pyrimidine HIV-1 NNRTIs DK6-1 is used in the preparation of drugs for treatment and prevention of HIV.

9. The thiophene[2,3-d]pyrimidine HIV-1 NNRTIs DK6-1 of claim 1, wherein the thiophene[2,3-d]pyrimidine HIV-1 NNRTIs DK6-1 is used for treating HIV.

10. The thiophene[2,3-d]pyrimidine HIV-1 NNRTIs DK6-1 of claim 1, wherein the thiophene[2,3-d] pyrimidine HIV-1 NNRTIs DK6-1 is used for preventing HIV.

11. A pharmaceutical composition consisting of thiophene[2,3-d]pyrimidine HIV-1 NNRTIs DK6-1 described in claim 1.

12. The pharmaceutical composition consisting of thiophene[2,3-d]pyrimidine HIV-1 NNRTIs DK6-1 described in claim 11 and its pharmaceutically acceptable vector.

13. The pharmaceutical composition consisting of thiophene[2,3-d]pyrimidine HIV-1 NNRTIs DK6-1 described in claim 11 and its medically acceptable excipients.

14. The thiophene[2,3-d]pyrimidine HIV-1 NNRTIs DK6-1 of claim 1, wherein the thiophene[2,3-d]pyrimidine HIV-1 NNRTIs DK6-1 is prepared as a drug for treating HIV.

15. The thiophene[2,3-d]pyrimidine HIV-1 NNRTIs DK6-1 of claim 14, the thiophene[2,3-d]pyrimidine HIV-1 NNRTIs DK6-1 is used for treating for AIDS in combination with NRTIs as the main component of HAART therapy.

* * * * *